United States Patent [19]
Sakamoto

[11] Patent Number: 5,869,642
[45] Date of Patent: Feb. 9, 1999

[54] DETECTION OF THE GENUS PECTINATUS

[75] Inventor: Kanta Sakamoto, Tokyo, Japan

[73] Assignee: Asahi Breweries, Ltd., Tokyo, Japan

[21] Appl. No.: 875,445

[22] PCT Filed: Nov. 27, 1996

[86] PCT No.: PCT/JP96/03464

§ 371 Date: Jul. 28, 1997

§ 102(e) Date: Jul. 28, 1997

[87] PCT Pub. No.: WO97/20071

PCT Pub. Date: Jun. 5, 1997

[30] Foreign Application Priority Data

Nov. 28, 1995 [JP] Japan .................................. 7-331172
Nov. 28, 1995 [JP] Japan .................................. 7-331173

[51] Int. Cl.$^6$ ............................. C07H 21/04; C12Q 1/68
[52] U.S. Cl. .................... 536/24.33; 435/6; 435/91.2; 536/24.3; 536/24.32; 935/77; 935/78
[58] Field of Search ................... 536/23.1, 24.32, 536/24.33; 435/6, 91.1, 91.2; 935/77, 78

[56] References Cited

U.S. PATENT DOCUMENTS 5,484,909 1/1996 Nietupski et al. .................... 536/24.32

OTHER PUBLICATIONS

Schleifer et al., Intl. J. Systematic Bacteriology 40(1):19–27, Jan. 1990.

Doyle et al., J. Industrial Microbiology 15:67–70, 1995.

*Primary Examiner*—Stephanie W. Zitomer
*Attorney, Agent, or Firm*—Wenderoth, Lind & Ponack, L.L.P.

[57] ABSTRACT

The present invention aims to provide a method for detecting a certain species of genus Pectinatus which is a beer-spoilage bacteria. An oligonucleotide characterized in that the oligonucleotide targets a nucleotide sequence coding a 16S ribosomal RNA gene of the genus Pectinatus to selectively detect a bacteria in a test sample, the oligonucleotide is complementary to the nucleotide sequence, and the oligonucleotide has a certain sequence groups, or at least one of the corresponding complementary sequence. A method for detecting the bacteria by using the oligonucleotide is also provided.

3 Claims, 3 Drawing Sheets

M: marker of molecular weight (φ X174/Hinc II)

1: *P.cerevisiiphilus*, primers (1) + (3)

2: *P.cerevisiiphilus*, primers (2) + (4)

3: *P.cerevisiiphilus*, primers (1) + (4)

4: *P.frisingensis*, primers (1) + (3)

5: *P.frisingensis*, primers (2) + (4)

6: *P.frisingensis*, primers (1) + (4)

M: marker of molecular weight ($\phi$ X174/Hinc II)

1: *P.cerevisiiphilus*, primers (5) + (7)

2: *P.cerevisiiphilus*, primers (6) + (8)

3: *P.cerevisiiphilus*, primers (5) + (8)

4: *P.frisingensis*,  primers (5) + (7)

5: *P.frisingensis*,  primers (6) + (8)

6: *P.frisingensis*,  primers (5) + (8)

M: marker of molecular weight (φ X174/Hinc II)

1: *Pectinatus cerevisiiphilus*,            primers (9) + (10)

2: *Pectinatus frisingensis*,              primers (9) + (10)

3: *Pectinatus* sp. DSM20764,          primers (9) + (10)

4: *Megasphaera cerevisiae* DSM20462, primers (9) + (10)

5: *Megasphaera cerevisiae* JCM6129,    primers (9) + (10)

6: *Selenomonas lacticifex*,               primers (9) + (10)

8: *Zymophilus paucivorans*,             primers (9) + (10)

9: *Zymophilus raffinosivorans*,         primers (9) + (10)

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:1:

CAGGCGGATG ACTAAGCG        18

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:2:

TGGGATTCGA ACTGGTCA        18

( 2 ) INFORMATION FOR SEQ ID NO:3:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:3:

CTCAAGATGA CCAGTTCG        18

( 2 ) INFORMATION FOR SEQ ID NO:4:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:4:

AATATGCATC TCTGCATACG        20

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:5:

CAGGCGGAAC ATTAAGCG 18

(2) INFORMATION FOR SEQ ID NO:6:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:6:

ATGGGGTCCG AACTGAGG 18

(2) INFORMATION FOR SEQ ID NO:7:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:7:

CTCAAGAACC TCAGTTCG 18

(2) INFORMATION FOR SEQ ID NO:8:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:8:

AATATCCATC TCTGGATACG 20

(2) INFORMATION FOR SEQ ID NO:9:

(i) SEQUENCE CHARACTERISTICS:
        (A) LENGTH: 18 bases
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:9:

TGGGGTCCGA ACTGAATG 18

(2) INFORMATION FOR SEQ ID NO:10:

(i) SEQUENCE CHARACTERISTICS:
        (A) LENGTH: 19 bases
        (B) TYPE: nucleic acid
        (C) STRANDEDNESS: single
        (D) TOPOLOGY: linear (ii) MOLECULE TYPE: oligonucleotides (xi) SEQUENCE DESCRIPTION: SEQ ID NO:10:

GCATCCATCT CTGAATGCG 19

(2) INFORMATION FOR SEQ ID NO:11:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:11:

CGCTTAGTCA TCCGCCTG      18

( 2 ) INFORMATION FOR SEQ ID NO:12:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:12:

TGACCAGTTC GAATCCCA      18

( 2 ) INFORMATION FOR SEQ ID NO:13:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:13:

CGAACTGGTC ATCTTGAG      18

( 2 ) INFORMATION FOR SEQ ID NO:14:

( i ) SEQUENCE CHARACTERISTICS:
    ( A ) LENGTH: 20 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:14:

CGTATGCAGA GATGCATATT      20

( 2 ) INFORMATION FOR SEQ ID NO:15:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:15:

CGCTTAATGT TCCGCCTG      18

( 2 ) INFORMATION FOR SEQ ID NO:16:

( i ) SEQUENCE CHARACTERISTICS:
    ( A ) LENGTH: 18 bases
    ( B ) TYPE: nucleic acid
    ( C ) STRANDEDNESS: single
    ( D ) TOPOLOGY: linear ( i i ) MOLECULE TYPE: oligonucleotides ( x i ) SEQUENCE DESCRIPTION: SEQ ID NO:16:

CCTCAGTTCG GACCCCAT                                                                                          18

( 2 ) INFORMATION FOR SEQ ID NO:17:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:17:

CGAACTGAGG TTCTTGAG                                                                                          18

( 2 ) INFORMATION FOR SEQ ID NO:18:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:18:

CGTATCCAGA GATGGATATT                                                                                        20

( 2 ) INFORMATION FOR SEQ ID NO:19:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:19:

CATTCAGTTC GGACCCCA                                                                                          18

( 2 ) INFORMATION FOR SEQ ID NO:20:

( i ) SEQUENCE CHARACTERISTICS:
        ( A ) LENGTH: 19 bases
        ( B ) TYPE: nucleic acid
        ( C ) STRANDEDNESS: single
        ( D ) TOPOLOGY: linear ( i i ) MOLECULE TYPE: oligonucleotides ( x i ) SEQUENCE DESCRIPTION: SEQ ID NO:20:

CGCATTCAGA GATGGATGC                                                                                         19

( 2 ) INFORMATION FOR SEQ ID NO:21:

( i ) SEQUENCE CHARACTERISTICS:
        ( A ) LENGTH: 1542
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        BIOLOGICAL NAME: Pectinatus SPECIES NAME: Pectinatus sp. DSM 20764

(x i) SEQUENCE DESCRIPTION: SEQ ID NO:21:

```
AGAGTTTGAT CCTGGCTCAG GACGAACGCT GGCGGCGTGC TTAACACATG CAAGTCGAAC      60
GGGACTTTTA TTTCGGTAAA AGTCTAGTGG CAAACGGGTG AGTAACGCGT AGGCAACCTA     120
CCTTCAAGAT GGGGACAACA TCCCGAAAGG GGTGCTAATA CCGAATGTTG TAAGAGTACT     180
GCATGGTACT TTTACCAAAG GCGGCTTTTA GCTGTTACTT GGAGATGGGC CTGCGTCTGA     240
TTAGCTAGTT GGTGACGGTA ATGGCGCACC AAGGCAACGA TCAGTAGCCG GTCTGAGAGG     300
ATGGACGGCC ACATTGGGAC TGAGACACGG CCCAGACTCC TACGGGAGGC AGCAGTGGGG     360
AATCTTCCGC AATGGGCGAA AGCCTGACGG AGCAACGCCG CGTGAACGAG GAAGGTCTTC     420
GGATCGTAAA GTTCTGTTGC AGGGGACGAA TGGCATTAGT GCTAATACCA CTAATGAATG     480
ACGGTACCCT GTTAGAAAGC CACGGCTAAC TACGTGCCAG CAGCCGCGGT AATACGTAGG     540
CGGCAAGCGT TGTCCGGAAT CATTGGGCGT AAAGGGAGCG CAGGCGGACA TTTAAGCGGA     600
TCTTAAAAGT GCGGGGCTCA ACCCCGTGAT GGGGTCCGAA CTGAATGTCT TGAGTGCAGG     660
AGAGGAAAGC GGAATTCCCA GTGTAGCGGT GAAATGCGTA GATATTGGGA AGAACACCAG     720
TGGCGAAGGC GGCTTTCTGG ACTGTAACTG ACGCTGAGGC TCGAAAGCCA GGGTAGCGAA     780
CGGGATTAGA TACCCCGGTA GTCCTGGCCG TAAACGATGG ATACTAGGTG TAGGGGGTAT     840
CGACCCCCCC TGTGCCGGAG TTAACGCAAT AAGTATCCCG CCTGGGGAGT ACGGCCGCAA     900
GGCTGAAACT CAAAGGAATT GACGGGGGCC CGCACAAGCG GTGGAGTATG TGGTTTAATT     960
CGACGCAACG CGAAGAACCT TACCAGGGCT TGACATTGAT TGACGCATTC AGAGATGGAT    1020
GCTTCCTCTT CGGAGGACAA GAAAACAGGT GGTGCATGGC TGTCGTCAGC TCGTGTCGTG    1080
AGATGTTGGG TTAAGTCCCG CAACGAGCGC AACCCCTATC ATTTGTTGCC AGCACGTAAC    1140
GGTGGGAACT CAAATGAGAC TGCCGCGGAC AACGCGGAGG AAGGCGGGGA TGACGTCAAG    1200
TCATCATGCC CCTTACGTCC TGGGCTACAC ACGTACTACA ATGGGATACA CAGAGGGAAG    1260
CAAAGGAGCG ATCCGGAGCG GAACCCAAAA AATATCCCCC AGTTCGGATT GCAGGCTGCA    1320
ACTCGCCTGC ATGAAGTCGG AATCGCTAGT AATCGCAGGT CAGCATACTG CGGTGAATAC    1380
GTTCCCGGGC CTTGTACACA CCGCCCGTCA CACCACGAAA GTCATTCACA CCCGAAGCCG    1440
GCTAAGGGCC TTATGGAACC GACCGTCTAA GGTGGGGGCG ATGATTGGGG TGAAGTCGTA    1500
ACAAGGTAGC CGTATCGGAA GGTGCGGCTG GATCACCTCC TT                       1542
```

DETECTION OF THE GENUS PECTINATUS

BACKGROUND OF THE INVENTION

1. Field of the Invention

The present invention relates to the detection of the genus Pectinatus which is known as beer spoilage bacteria. More particularly, the present invention relates to a gene sequence for detecting *Pectinatus cerevisiiphilus, Pectinatus frisingensis* and Pectinatus sp. DSM20764, respectively, and to a method for detecting the bacteria by using the sequence.

2. Description of the Related Art

Presently, in a method for testing micro-organisms in the field of beer production and, for identifying the species, the bacteria must be separated via growth cultivation and segregation cultivation, which takes at least seven days. Then the, separated bacteria is propagated, and the identification is conducted by many tests such as observation of the form and Gram stain properties, a catalase test, and presence of sugar consumption. These troublesome tests require many hours and the tests are expensive. In addition to these conventional identification methods, there is a method for identifying species by a hybridization test, in which DNA is extracted from an isolated bacteria and the DNA is fixed on a membrane or other substrate, and detected with the DNA of a standard bacteria as a probe. However, this method takes several days, and it is difficult to obtain the necessary detection sensitivity.

Recently, for detecting a bacteria quickly, there is a method for detecting a living bacteria by an ATP luminescence method using reported in J. Am. Soc. Brew. Chem.: 52(1) 19–23, 1994. But this method is unable to identify the species. Further, for a part of lactic acid bacteria, for example, *Lactobacillus brevis, Lactobacillus plantarum* and *Lactobacillus coryniformis,* as disclosed in Japanese Patent Laid-open Publication Nos. 6-46811(1994) and 6-311894 (1994), it is possible to identify the species at a relatively early stage by using antibodies specific for each species. However, to apply the method, operation for isolating the bacteria is still required. Accordingly, it takes more several days, and it is difficult to obtain sufficient detection sensitivity and selectivity.

More quick detection methods have been studied, lately, as disclosed in Japanese Patent Laid-open Publication Nos. 5-15400(1993) and 6-141899(1994), and as reported in J. Am. Soc. Brew. Chem.: 52(3) 95–99, 1994, there is a method for detecting the lactic acid bacteria, wherein the DNA of lactic acid bacteria is extracted to serve as a sample and an oligonucleotide complementary for the DNA is functionally used as a primer.

On the other hand, lately, it is confirmed that the genus Pectinatus of an obligately anaerobic bacterium exerts a bad influence on the product beer. To detect the genus, a selective separation medium was examined (J. Am. Soc. Brew. Chem.: 52(3) 115–119, 1994), a group for determining the main antigen was identified by using an immunoblotting technique (FEMS. MICROBIOL. LETT.: 67(3) 307–311, 1990), and a method using a fluoroimmunoassay method was disclosed (J. Am. Soc. Brew. Chem.: 51(4) 158–163, 1993). However, satisfactory methods are not established in aspects of the detectable sensitivity, detection times and the like.

The present invention aims to develop a method wherein the genus Pectinatus is more quickly and sensitively detected and identified at the same time.

SUMMARY OF THE INVENTION

The present invention provides a method wherein oligonucleotides specifically hybridizing with 16S ribosomal genes of the genus Pectinatus are prepared. These oligonucleotides are then used for gene amplification by functioning as a primer, and each bacteria is selectively detected.

The oligonucleotides specifically hybridizing *Pectinatus cerevisiiphilus* have at least one of the following sequence groups:

5'-CAGGCGGATGACTAAGCG-3' (1) (SEQ ID NO. 1)
5'-TGGGATTCGAACTGGTCA-3' (2) (SEQ ID NO. 2)
5'-CTCAAGATGACCAGTTCG-3' (3) (SEQ ID NO. 3)
5'-AATATGCATCTCTGCATACG-3' (4) (SEQ ID NO. 4)

or at least one of the corresponding complementary sequence groups:

5'-CGCTTAGTCATCCGCCTG-3' to the sequence of (1) (SEQ ID NO. 11)
5'-TGACCAGTTCGAATCCCA-3' to the sequence of (2) (SEQ ID NO. 12)
5'-CGAACTGGTCATCTTGAG-3' to the sequence of (3) (SEQ ID NO. 13)
5'-CGTATGCAGAGATGCATATT-3' to the sequence of (4) (SEQ ID NO. 14)

Further, the oligonucleotides specifically hybridizing *Pectinatus frisingensis* have at least one of the following sequence groups:

5'-CAGGCGGAACATTAAGCG-3' (5) (SEQ ID NO. 5)
5'-ATGGGGTCCGAACTGAGG-3' (6) (SEQ ID NO. 6)
5'-CTCAAGAACCTCAGTTCG-3' (7) (SEQ ID NO. 7)
5'-AATATCCATCTCTGGATACG-3' (8) (SEQ ID NO. 8)

or at least one of the corresponding complementary sequence groups:

5'-CGCTTAATGTTCCGCCTG-3' to the sequence of (5) (SEQ ID NO. 15)
5'-CCTCAGTTCGGACCCCAT-3' to the sequence of (6) (SEQ ID NO. 16)
5'-CGAACTGAGGTTCTTGAG-3' to the sequence of (7) (SEQ ID NO. 17)
5'-CGTATCCAGAGATGGATATT-3' to the sequence of (8) (SEQ ID NO. 18).

Then, the oligonucleotides, which target a nucleotide sequence coding a 16S ribosomal RNA gene of Pectinatus sp. DSM20764 and are complementary to the sequence nucleotide, have at least one of the following sequence groups:

5'-TGGGGTCCGAACTGAATG-3' (9) (SEQ ID NO. 9)
5'-GCATCCATCTCTGAATGCG-3' (10) (SEQ ID NO. 10)

or at least one of the corresponding complementary sequence groups:

5'-CATTCAGTTCGGACCCCA-3' to the sequence of (9) (SEQ ID NO. 20)
5'-CGCATTCAGAGATGGATGC-3' to the sequence of (10) (SEQ ID NO. 20).

In addition, the present invention provides DNA containing the whole base sequences or at least ten continuous base sequences of the gene coding for the 16S ribosomal RNA gene of Pectinatus sp. DSM20764. Then, the whole base sequences aforesaid are shown by the sequence No.21 undermentioned. The Pectinatus sp. DSM20764 is obtainable from DSM-Deutche Sammlung von Mikroorganismen und Zellkulturen GmbH.

The technique concerning gene amplification has been known, and it can be done using a Polymerase Chain Reaction method (abbreviated as an PCR method hereinafter; Science 230, 1350, 1985). This reaction aims to amplify a special gene sequence. This method has been applied in the field of genetic study, lately in the medical field for rapid determination of viruses, and in the food field for rapid detection of bacteria, because it shows rapid and high sensitivity and high specificity. By the PCR method, even though small amount of the target gene is in a sample, the target sequence between two primers is a amplified several millions times, and detectable copies are produced in large quantities. In the PCR method, it is necessary to release the component of nucleic acid. When the sample has no less than several molecules, the amplification reaction proceeds, so that PCR can be done only by simple pretreatment using a lytic enzyme or a surfactant. Accordingly, the PCR method is very useful in comparison with conventional bacteria detection methods.

To use these methods, the present invention has been developed. In the present invention, the PCR method is conducted by using as an primer the oligonucleotide which is designed to hybridize specifically with 16S ribosomal genes of Pectinatus cerevisiiphilus, Pectinatus frisingensis and Pectinatus sp. DSM20764, so that the sequence to be recognized is detected, and it is able to decide whether the bacteria of Pectinatus cerevisiiphilus, Pectinatus frisingensis or Pectinatus sp. DSM20764 is present or not in the sample, rapidly and sensitively. The sample may be collected from beer or green beer in the brewing process or a sample from sewage in an anaerobic atmosphere. Further, the oligonucleotide used as a primer may be obtained by chemical synthesis or from natural products.

The base length of the target sequence the nucleotide sequence of the 16S ribosomal RNA gene of Pectinatus cerevisiiphilus, which is specified by two primers, is about 70 base pairs in combination with primers 1 and 3, about 390 base pairs in combination with primers 2 and 4, and 440 base pairs in combination with primers 1 and 4. Since any combination of these primers is specific for Pectinatus cerevisiiphilus, it is possible to detect the species, and it is possible to identify more reliably by using two or more combination of primers in parallel.

The base length of the target sequence the nucleotide sequence of the 16S ribosomal RNA gene of Pectinatus frisingensis, which is specified by two primers, is about 70base pairs in combination with primers 5 and 7, about 390 base pairs in combination with primers 6 and 8, and 440 base pairs in combination with primers 5 and 8. Since any combination of these primers is specific for Pectinatus frisingensis, it is possible to detect the genus, and it is possible to identify more reliably by using two or more combination of primers in parallel.

The base length of the target sequence on the nucleotide sequence of the 16S ribosomal RNA gene of Pectinatus sp. DSM20764, which is specified by two primers 9 and 10, is about 390 base pairs. Since the combination of these primers is specific for Pectinatus sp. DSM20764, it is possible to detect the genus.

The DNA polymerase thermostable at a temperature of 90° C. or more may be used in the PCR. The temperature conditions for one cycle of PCR is 90°–98° C. in the thermal denaturalizing reaction for changing a double strand DNA into a single strand DNA, 37°–65° C. in the annealing reaction to hybridize primers with DNA at templates, and 50°–75° C. in the elongation reaction to act a DNA polymerase. Several cycles are conducted to amplify target sequences. After the PCR, the reaction products are separated by electrophoresis. The nucleic acids of the resulting products are stained by ethidium bromide and the like. When the base length of the amplified nucleotide sequence is equal to the base length of the above target sequence, the presence of Pectinatus cerevisiiphilus, Pectinatus frisingensis or Pectinatus sp. DSM20764 is decided. The amplified nucleotide sequence is also effectively detected by chromatography.

DETAILED DESCRIPTION OF THE PREFERRED EMBODIMENTS

Figure 1:
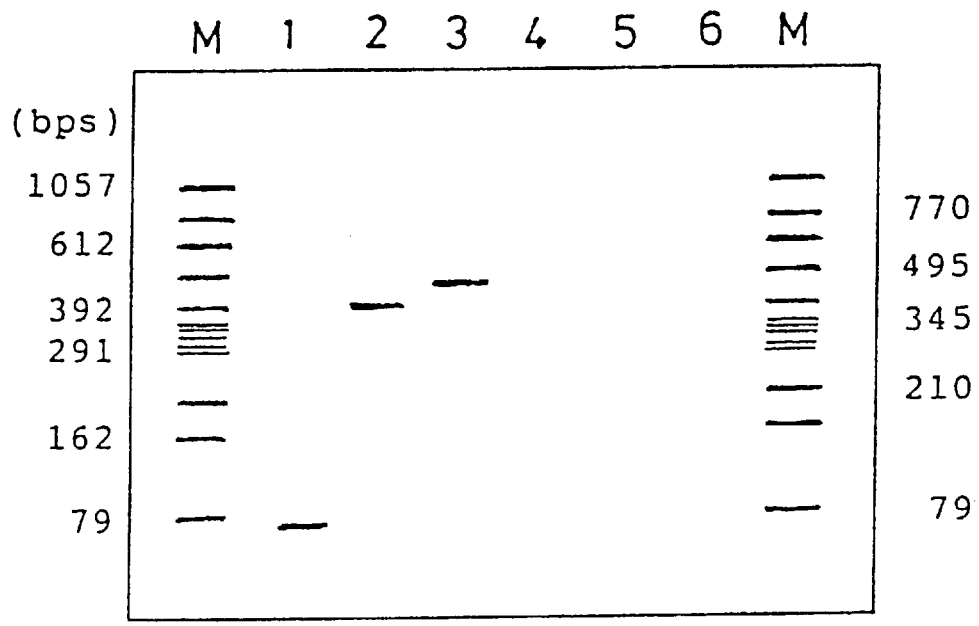
FIG. 1 shows a result of electrophoresis after the PCR of the samples of bacteria Nos. 2 and 5 in Table 1, in combination with primers 1–4.

The following examples serve to illustrate the present invention. (1) Detection method of Pectinatus cerevisiiphilus Preparation of Samples Ten strains of three kinds of bacterial types of Pectinatus in Table 1 were used. To confirm the specificity of primers for Pectinatus cerevisiiphilus, bacteria and yeasts to be detected except the Pectinatus in the inspection of beer microorganisms, and the E. coli used often in laboratories were used. After cultivating these strains at suitable cultures for amplification, the strains were collected by centrifugation. Then, the DNA from the strains were extracted in accordance with the description of SHIN-SEIKAGAKU-JIKKEN-KOZA 2, Nucleic acid I, Separation and Purification, page 20–21 (edited by Japan Biochemical Learned Society, Tokyo-Kagaku-Dojin) to obtain each one ml of DNA solution.

TABLE 1

| Bacteria No. | Bacteria type | Name of strain | Remarks |
|---|---|---|---|
| 1 | pectinatus cerevisiiphilus | DSM20466 | |
| 2 | pectinatus cerevisiiphilus | DSM20467 | type strain, ATCC29359 |
| 3 | pectinatus cerevisiiphilus | DSM20762 | |
| 4 | pectinatus cerevisiiphilus | DSM20763 | |
| 5 | pectinatus frisingensis | DSM6036 | type strain, ATTC33332 |
| 6 | pectinatus frisingensis | DSM20465 | |
| 7 | pectinatus frisingensis | DSM20759 | |
| 8 | pectinatus frisingensis | DSM20760 | |
| 9 | pectinatus frisingensis | DSM20761 | |
| 10 | Pectinatus sp. | DSM20764 | |
| 11 | Lactobacillus brevis | JCM1059 | type strain |
| 12 | Lactobacillus casei | ATCC334 | type strain |
| 13 | Lactobacillus coryniformis | JCM1164 | type strain |
| 14 | Lactobacillus lindneri | DSM20690 | type strain |
| 15 | Lactobacillus plantarum | JCM1149 | type strain |
| 16 | Lactococcus lactis | JCM5805 | type strain |
| 17 | Lactococcus lactis | JCM6123 | type strain |
| 18 | Pediococcus damnosus | JCM5886 | type strain |
| 19 | Megasphaera cerevisiae | DSM20462 | type strain |
| 20 | Megasphaera cerevisiae | JCM6129 | |
| 21 | Zymophilus raffinosivorans | DSM20765 | type strain |
| 22 | Zymophilus paucivorans | DSM20756 | type strain |
| 23 | Saccharomyces cerevisiae | 1 | beer brewer's yeast |
| 24 | Saccharomyces cerevisiae | 2 | beer brewer's yeast |
| 25 | Saccharomyces cerevisiae | 3 | beer brewer's yeast |
| 26 | Escherichia coli | K-12 | |

Synthesis of Primers

Referring to the base sequences of 16S ribosomal RNA genes of Pectinatus cerevisiiphilus (KARL HEINZ SCHLEIFER, and HELGA SEIDEL-RUFER et al, Int. J. Syst. Bact eriol. 40(1): 19–27, 1990), the following sequence group of 1–4 was selected, and oligonucleotides having the same sequences were chemically synthesized.
5'-CAGGCGGATGACTAAGCG-3' (1)
5'-TGGGATTCGAACTGGTCA-3' (2)
5'-CTCAAGATGACCAGTTCG-3' (3)
5'-AATATGCATCTCTGCATACG-3' (4)

PCR

To a sterilized tube of 0.5 ml, the above sample solution of 1 μl, sterilized water of 78.5 μl, 10× buffer for reaction of 10 μl (manufactured by Toyobo Co., Ltd., 10× TAP), 6 μl of water solution of 25 mM magnesium chloride, one μl of 20 mM dNTPs, each one μl of 100 μM of primer 1 and 100 μM of primer 3 (or Primers 2 and 4, or 1 and 4), and 0.5 μl of 5U/μl Taq DNA polymerase (manufactured by Toyobo Co., Ltd., TAP-101) were added, and 100 μl of reaction solution was prepared. PCR was repeated for 30 cycles, and one cycle had the following temperature conditions:
thermal denaturalizing; 94° C. for one minute,
annealing; 54° C. for one minute and
elongation reaction; 74° C. for one minute.

Before the cycle reaction, the solution was reacted at a temperature of 98° C. for one minute. At the end of the reaction, the solution was treated to heat at 74° C. for three minutes. The program tempcontrol system PC-800 manufactured by ASTEC company was used as a thermal control unit.

Detection

Using 10 μl of reaction solution after the PCR, electrophoresis was conducted by 3.5% (w/v) agarose gel at 100V constant voltage for 30 minutes. At the same time, øX174/HincII was electrophoresed as a molecular weight marker. After the electrophoresis, the gel was dyed in a ethidium bromide solution (about 0.5 μg/ml) for 15 minutes, the gel was observed under ultraviolet irradiation, and photographed. By the observation or photograph of the gel, the base length of the amplified products was determined from relative migration distance to the molecular weight marker.

Result

The result of the electrophoresis of the samples of bacteria numbers 2 and 5 in Table 1 after the PCR was shown in FIG. 1. The result of detected bands of all tested bacteria was shown in Table 2.

TABLE 2

| Bacteria No. | Combination of primers | | |
|---|---|---|---|
| | 1 + 3 | 2 + 4 | 1 + 4 |
| 1 | 0.07 | 0.39 | 0.44 |
| 2 | 0.07 | 0.39 | 0.44 |
| 3 | 0.07 | 0.39 | 0.44 |
| 4 | 0.07 | 0.39 | 0.44 |
| 5–26 | — | — | — |

In the table, figures show base length (kilo base pairs) of detected bands, and (–) shows no band.

From the result, when each oligonucleotide of sequences of the above 1–4 was used as a primer of the PCR in the combination as shown in Table 2, a band of only *Pectinatus cerevisiiphilus* DNA was detected, and the band showed a figure of the base equal to that of the target sequence. Therefore, it is shown that each oligonucleotide of the present invention properly recognizes the sequence targeted by the 16S ribosomal RNA gene of *Pectinatus cerevisiiphilus*. Since no band was detected by the other genus including *Pectinatus frisingensis*, in the present invention, it was certified that *Pectinatus cerevisiiphilus* can be specifically detected, and it can be identified.

(2) Detection method of *Pectinatus frisingensis*

Preparation of Samples

Ten strains of three kinds of bacterial species of Pectinatus as shown in Table 1 were used by the same method as described above. To confirm the specificity of primers for *Pectinatus frisingensis*, bacteria and yeasts to be detected except the Pectinatus in the inspection of beer microorganisms, and the *E. coli* used often in laboratories were used. After cultivating these strains at suitable cultures for amplification, the strains were collected by centrifugation. Then, the DNA from the strains were extracted in accordance with the description of SHIN-SEIKAGAKU-JIKKEN-KOZA 2, Nucleic acid I, Separation and Purification, page 20–21 (edited by Japan Biochemical Learned Society, Tokyo-Kagaku-Dojin) to obtain each one ml of DNA solution.

Synthesis of Primers

From the base sequences of 16S ribosomal RNA genes of *Pectinatus frisingensis* (KARL HEINZ SCHLEIFER, and HELGA SEIDEL-RUFER et al, Int. J. Syst. Bacteriol. 40(1): 19–27, 1990), the following sequence group of 5–8 were selected, and oligonucleotides having the same sequences was chemically synthesized.

5'-CAGGCGGAACATTAAGCG-3' (5)
5'-ATGGGGTCCGAACTGAGG-3' (6)
5'-CTCAAGAACCTCAGTTCG-3' (7)
5'-AATATCCATCTCTGGATACG-3' (8)

PCR

To a sterilized tube of 0.5 ml, the above sample solution of 1 μl, sterilized water of 78.5 μl, 10× buffer for reaction of 10 μl (manufactured by Toyobo Co., Ltd., 10× TAP), 6 μl of water solution of 25 mM magnesium chloride, one μl of 20 mM dNTPs, each one μl of 100 μM of primer 5 and 100 μM of primer 7 (or Primers 6 and 8, or 5 and 8), and 0.5 μl of 5U/μl Taq DNA polymerase (manufactured by Toyobo Co., Ltd., TAP-101) were added, and 100 μl of reaction solution was prepared. PCR was repeated for 30 cycles, and one cycle had the following temperature conditions:
thermal denaturalizing; 94° C. for one minute,
annealing; 54° C. for one minute and
elongation reaction; 74° C. for one minute.

Before the cycle reaction, the solution was reacted at a temperature of 98° C. for one minute. After the conclusion of the reaction, the solution was treated to heat at 74° C. for three minutes. The program tempcontrol system PC-800 manufactured by ASTEC company was used as a thermal control unit.

Detection Using 10 μl of reaction solution after the PCR, electrophoresis was conducted by 3.5% (w/v) agarose gel at 100V constant voltage for 30 minutes. At the same time, øX174/HincII was electrophoresed as a molecular weight marker. After the electrophoresis, the gel was dyed in a ethidium bromide solution (about 0.5 μg/ml) for 15 minutes, the gel was observed under ultraviolet irradiation, and photographed. By the observation or photograph of the gel, the base length of the amplified products was determined from relative migration distance to the molecular weight marker.

Result

Figure 2:
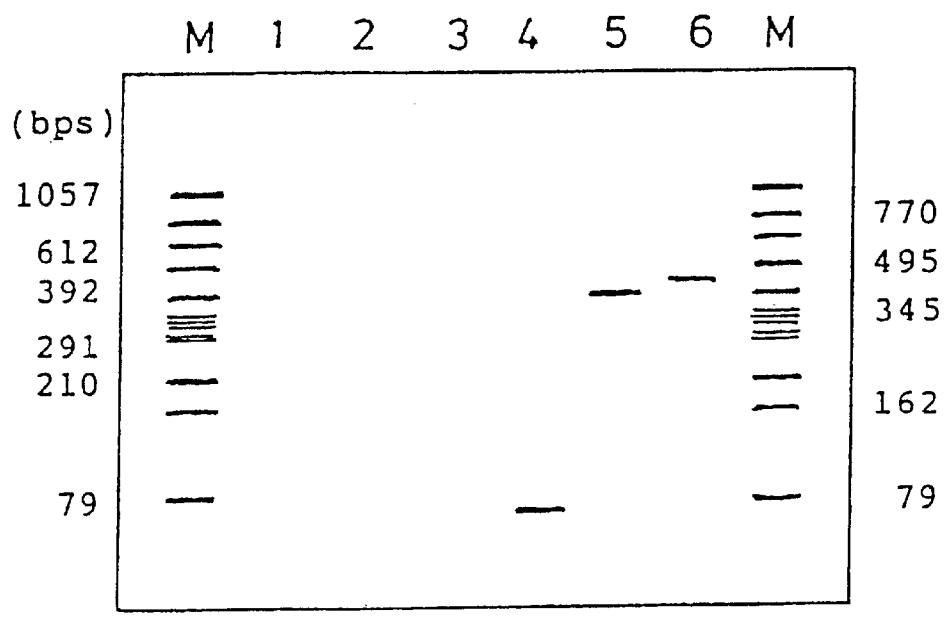
FIG. 2 shows a result of electrophoresis after the PCR reaction of the samples of bacteria Nos. 2 and 5 in Table 1, in combination with primers 5–8.

The result of the electrophoresis of the samples of bacteria numbers 2 and 5 in Table 1 after the PCR was shown in FIG. 2.

The result of detected bands of all tested bacteria was shown in Table 3.

TABLE 3

| Genus No. | Combination of primers | | |
|---|---|---|---|
| | 5 + 7 | 6 + 8 | 5 + 8 |
| 1 | — | — | — |
| 2–4 | — | — | — |
| 5 | 0.07 | 0.39 | 0.44 |
| 6 | 0.07 | 0.39 | 0.44 |
| 7 | 0.07 | 0.39 | 0.44 |

TABLE 3-continued

| | Combination of primers | | |
|---|---|---|---|
| Genus No. | 5 + 7 | 6 + 8 | 5 + 8 |
| 8 | 0.07 | 0.39 | 0.44 |
| 9 | 0.07 | 0.39 | 0.44 |
| 10–26 | — | — | — |

In the table, figures show base length (kilo base pairs) of detected bands, and (–) shows no band.

From the result, when each oligonucleotide of sequences of the above 5–8 was used as a primer of the PCR in the combination as shown in Table 3, a band of only *Pectinatus frisingensis* DNA was detected and the band showed a figure of the base equal to that of the target sequence. Therefore, it is shown that each oligonucleotide of the present invention properly recognizes the sequence targeted by the 16S ribosomal RNA gene of *Pectinatus frisingensis*. Since no band was detected by the other genus including *Pectinatus cerevisiiphilus,* in the present invention, it was certified that *Pectinatus frisingensis* can be specifically detected, and it can be identified.

(3) Detection method of Pectinatus sp. DSM20764

Preparation of Samples In the Pectinatus, *Pectinatus cerevisiiphilus* (DSM20467), *Pectinatus frisingensis* (DSM6306) and Pectinatus sp. DSM20764 were used. To confirm the specificity of the primer of Pectinatus sp. DSM20764, other bacteria of obligate anaerobic bacteria as shown in Table 4 were used. After cultivating these bacteria at suitable cultures for amplification, the strains were collected by centrifugation. Then, the DNA from the strains were extracted in accordance with the description of SHIN-SEIKAGAKU-JIKKEN-KOZA 2, Nucleic acid I, Separation and Purification, page 20–21 (edited by Japan Biochemical Learned Society, Tokyo-Kagaku-Dojin) to obtain the DNA solution.

TABLE 4

| Bacteria No. | Bacteria type | Name of strain | Remarks |
|---|---|---|---|
| 1 | Pectinatus cerevisiiphilus | DSM20467 | type strain |
| 2 | Pectinatus frisingensis | DSM6306 | type strain |
| 3 | Pectinatus sp. | DSM20764 | |
| 4 | Megasphaera cerevisiae | DMS20462 | type strain |
| 5 | Megasphaera cerevisiae | JCM6129 | |
| 6 | Megasphaera elsdenii | JCM1772 | type strain |
| 7 | Selenomonas lacticifex | DSM20757 | type strain |
| 8 | Zymophilus paucivorans | DSM20756 | type strain |
| 9 | Zrmophilus raffinosivorans | DSM20765 | type strain |

Determination of the base sequence of the 16S ribosomal RNA gene of Pectinatus sp. DSM20764

Using the DNA solution of the Pectinatus sp. DSM20764 prepared as described above as a template, PCR was conducted by the primer attaching a M13 primer sequence to the 5' side of a universal primer in common with many bacteria, which was described in Modern Microbiological Methods' Nucleic Acid Techniques in Bacterial Systematics' "16S/23S rRNA Sequencing" p115–175 (J. Wiley & Sons Ltd., New York).

After the PCR, amplified DNA fragments were separated by agarose electrophoresis cut from the gel eluted from the gel using a spin column (for collecting DNA from gel, Trade name SUPREC™-01 manufactured by Takara Shuzo, and recovered by ethanol precipitate. Using the resulting DNA fragments as a template, the sequence reaction was conducted. An infrared dye labeled Forward Primer M13, Trade name IRD41 manufactured by Nisshinbo, and sold by Aroka Ltd., Co. was used as a sequencing primer, and a sequencing kit (Trade name SEQUITHERM™ Long-Read™ Cycle Sequencing Kit-LC manufactured by EPICENTRE TECHNOLOGIES Company was used as reaction solution. The base sequence was determined by a laser system (for reading DNA sequences, Trade name 4000L Long READIR™ DNA Sequencing System manufactured by LI-COR company.

The resulting 16S ribosomal RNA gene sequence of the Pectinatus sp. DSM20764 is shown in sequence No. 21.

Synthesis of Primer

Oligonucleotides, which had the same sequence as that of No. 630 to No. 647 on the sequence of the 16S ribosomal RNA gene of the Pectinatus sp. DSM20764 in sequence No. 21, and oligonucleotide, which had a complementary sequence to that of No. 1004 to No. 1022, were chemically synthesized.

Detection and identification of Pectinatus sp. DSM20764 using a primer

The PCR of DNA solution of each bacterium obtained by preparation of samples was conducted by using the synthesized oligonucleotides. The PCR was repeated for 35 cycles, and one cycle had the following temperature conditions:

thermal denaturalizing; 94° C. for 30 seconds, annealing; 55° C. for 80 seconds and elongation reaction; 72° C. for 30 seconds.

After the conclusion of the PCR, the solution was electrophoresed by agarose gel at 100V constant voltage for 30 minutes. At the same time, ø X174/HincII was electrophoresed as a molecular weight marker. After the electrophoresis, the gel was dyed in a ethidium bromide solution (about 0.5 μg/ml) for 15 minutes, the gel was observed under ultraviolet irradiation, and photographed. By the observation or photograph of the gel, the base length of the amplified products was determined from relative migration distance to the molecular weight marker.

Figure 3:
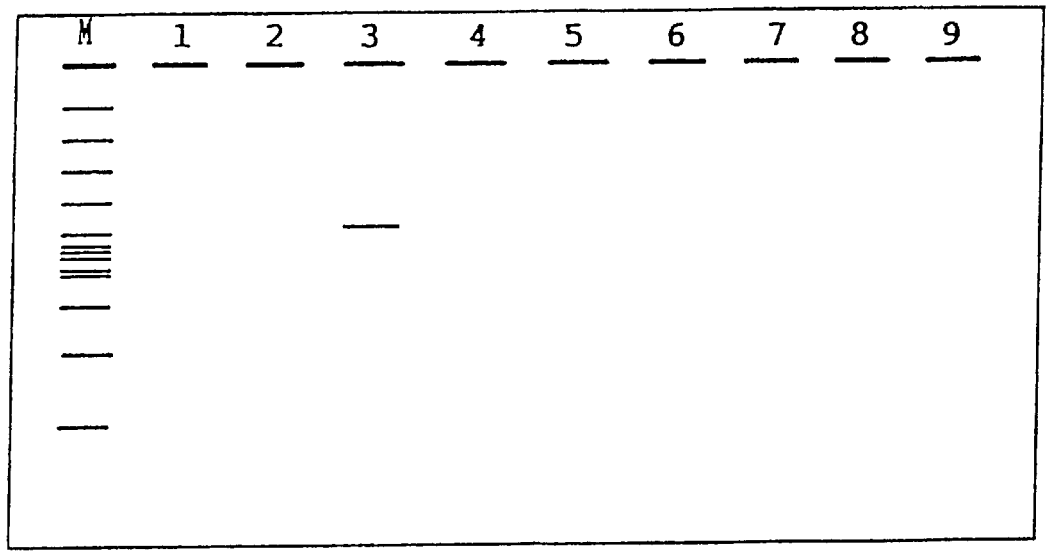
FIG. 3 shows a result of electrophoresis after the PCR of the samples of bacteria Nos. 1–9 in Table 4, in combination with primers 9 and 10.

From the result, as shown in FIG. 3, about 890 bps of a band of only Pectinatus sp. DSM20764 DNA was detected. When the above oligonucleotide was used as a primer of the PCR, a band having the object length of only Pectinatus sp. DSM20764 DNA was detected. Therefore, it is shown that each oligonucleotide of the present invention properly recognizes the sequence targeted by the 16S ribosomal RNA gene of Pectinatus sp. DSM20764. Since no band was detected by the same genus including *Pectinatus cerevisiiphilus* and *Pectinatus frisingensis,* in the present invention, it was certified that Pectinatus sp. DSM20764 can be specifically detected, and it can be identified.

Industry Applicability

It takes conventionally at least ten days to identify the kind of Pectinatus. On the other hand, in the present invention, preculture and separation culture of the one not always needed. Within one to three days, quickly and reliably, it is possible to detect and identify *Pectinatus cerevisiiphilus, Pectinatus frisingensis* and Pectinatus sp. DSM20764 in the sample. Further, since the PCR method can be easily conducted, a skilled operator is unnecessary. It is possible to detect in high reliability and low cost. By great progress of the PCR peripheral apparatus, it becomes possible to automatically detect the Pectinatus in the present invention.

I claim:

1. An oligonucleotide comprising a sequence selected from the group consisting of SEQ ID NO.:1, SEQ ID NO.:2, SEQ ID NO.:3, SEQ ID NO.:4, SEQ ID NO.:11, SEQ ID NO.:12, SEQ ID NO.:13 and SEQ ID NO.:14.

2. An oligonucleotide comprising a sequence selected from the group consisting of SEQ ID NO.:5, SEQ ID NO.:6, SEQ ID NO.:7, and SEQ ID NO.:8, SEQ ID NO.:15, SEQ ID NO.:16, SEQ ID NO.:17, and SEQ ID NO.:18.

3. An oligonucleotide comprising a sequence selected from the group consisting of SEQ ID NO. :9 and SEQ ID NO. :10, SEQ ID NO.:19 and SEQ ID NO.:20.

* * * * *